United States Patent [19]

Prücher et al.

[11] Patent Number: 5,714,502
[45] Date of Patent: Feb. 3, 1998

[54] PIPERIDINYLMETHYLOXAZOLIDINONES

[75] Inventors: Helmut Prücher, Heppenheim; Gerd Bartoszyk, Weiterstadt, both of Germany

[73] Assignee: Merck Patent Gesellschaft mit beschrankter Haftung, Darmstadt, Germany

[21] Appl. No.: 701,852

[22] Filed: Aug. 23, 1996

[30] Foreign Application Priority Data

Aug. 25, 1995 [DE] Germany .................. 195 31 321.6

[51] Int. Cl.⁶ .................. A61K 31/445; C07D 413/06
[52] U.S. Cl. .................. 514/326; 546/209
[58] Field of Search .................. 546/209; 514/326

[56] References Cited

U.S. PATENT DOCUMENTS

| | | | |
|---|---|---|---|
| 4,804,657 | 2/1989 | Kogure | 514/218 |
| 4,970,217 | 11/1990 | Prücher et al. | 514/327 |
| 5,232,931 | 8/1993 | Prücher | 514/321 |
| 5,561,145 | 10/1996 | Prücher et al. | 514/327 |

FOREIGN PATENT DOCUMENTS

| | | |
|---|---|---|
| 2 036 586 | 8/1991 | Canada . |
| 43 24 393.2 | 7/1993 | Germany . |

OTHER PUBLICATIONS

CA111: 7390w Preparation of . . . agents. Prucher et al., p. 710, 1989.

*Primary Examiner*—Joseph McKane
*Attorney, Agent, or Firm*—Millen, White, Zelano, & Branigan, P.C.

[57] ABSTRACT

The invention relates to novel piperidinylmethyloxazolidin-2-one derivatives of the formula I

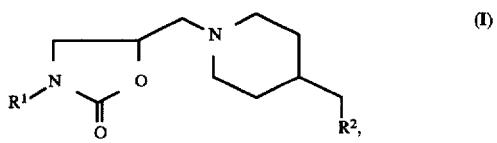

in which $R^1$ and $R^2$ in each case independently of one another are unsubstituted or mono- to disubstituted phenyl radicals whose substituents can be A, OA, aryloxy having 6–10 C atoms, aralkyloxy having 7–11 C atoms, —O—$(CH_2)_n$—O— (bonded in directly adjacent positions or in the meta- or para-position to one another on the phenyl ring), —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$ (excluding $R^3=SO_2A$), $SO_2N(R^3)_2$ (excluding $R^3=SO_2A$) or $R^3$, $R^3$ is COH, CO-alkyl having 1–7 C atoms in the alkyl, CO-alkyl-Ar having 8–12 C atoms, CO-Ar having 7–13 C atoms, $SO_2A$ A is an alkyl radical having 1–6 C atoms n is 1 or 2

Hal is F, Cl, Br or I and their physiologically acceptable salts.

19 Claims, No Drawings

PIPERIDINYLMETHYLOXAZOLIDINONES

SUMMARY OF THE INVENTION

The invention relates to novel piperidinylmethyloxazolidin-2-one derivatives of the formula I

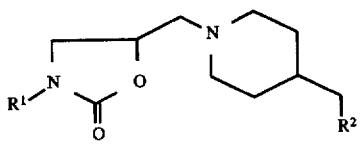

(I)

in which

R$^1$ and R$^2$ in each case independently of one another are unsubstituted or mono- to disubstituted phenyl radicals whose substituents can be A, OA, aryloxy having 6–10 C atoms, aralkyloxy having 7–11 C atoms, —O—(CH$_2$)$_n$—O— (bonded in directly adjacent positions or in the meta- or para-position to one another on the phenyl ring), —O—(CH$_2$)$_n$—OH, Hal, CF$_3$, OH, NO$_2$, NH$_2$, NHA, NA$_2$, NHR$^3$, NAR$^3$, SO$_2$NH$_2$, SO$_2$NHA, SO$_2$NA$_2$, SO$_2$NHR$^3$ (excluding R$^3$=SO$_2$A), SO$_2$N(R$^3$)$_2$ (excluding R$^3$=SO$_2$A) or R$^3$.

R$^3$ is COH, CO-alkyl having 1–7 C atoms in the alkyl portion, CO-alkyl-aryl having 8–12 C atoms in the alkyl and aryl portions, CO-aryl having 7–13 C atoms in the aryl portion, or SO$_2$A A is an alkyl radical having 1–6 C atoms n is 1 or 2

Hal is F, Cl, Br or I and their physiologically acceptable salts. The invention also relates to the preparation of these novel compounds and their use as psychopharmacologically active substances.

Besides a large number of possible other compounds, the application DE 4005371 A1 also generally describes piperidinylalkyloxazolidinones as pharmaceutically active compounds in which an oxazolidinone ring substituted on the nitrogen in the 5-position is bonded either via an ethyl or a propyl group to the nitrogen of a likewise substituted piperidine ring. According to this application, properties relating to an effect on the central nervous system were found for such compounds.

The Application DE 43 24 393 A1 also describes piperidinylalkyloxazolidinones which have an action, in particular a neuroleptic action, affecting the central nervous system without a noticeable cataleptic action occurring. In this case, these are piperidine derivatives which are substituted in the 4-position by aryloxy or arylthio groups.

The object of the invention was therefore to make available novel compounds which can be used for the production of medicaments, but compared with the active compounds already known have a more pronounced spectrum of action and act selectively on the central nervous system, have few side effects, also can be administered in the lowest possible dose on account of a modified structure and also do not have or only have a very low dependence potential.

It has now been found that the compounds of the formula I and their physiologically acceptable salts have useful pharmacological properties combined with good tolerability. They particularly affect the central nervous system and have sedative, tranquillizing, neuroleptic and/or antidepressant actions without a noticeable cataleptic action being detectable.

The invention therefore relates to the novel piperidinylmethyloxazolidin-2-one derivatives of the given formula I and their salts and use thereof as pharmacologically active substances.

The invention also relates, however, to suitable processes for the preparation of these compounds and their salts.

The compounds of the given formula I and their salts specifically have a damping action on behavior in the case of mice (Methodology cf. Irwin, Psychopharmacologica 13 (1968), 222–257). In mice, they inhibit the climbing behavior induced by apomorphine (methodology cf. Costall et al., European J. Pharmacol. 50 (1968), 39–50) or induced contralateral pivoting behavior in hemiparkinson rats (detectable by the method of Ungerstedt et al., Brain Res. 24 (1970), 485–493) without noticeable cataleptic side effects occurring (Methodology cf. Dolini-Stola, Pharmakopsychiat. 6 (1973), 189–197). These active compounds also inhibit the binding of tritiated dopamine agonists and antagonists to extraparamidal receptors (detectable by the method of Schwarcz et al., J. Neurochemistry 34 (1980), 772–778, and Creese et al., European J. Pharmacol. 46 (1977), 377–381). The compounds furthermore inhibit the linguomandibular reflex in the anaesthetized rat (detectable following the methods of Barnett et al., European. J. Pharmacol. 21 (1973), 178–182, and of Ilhan et al., European J. Pharmacol. 33 (1975), 61–64). In addition, analgesic and hypotensive actions are detectable; i.e. in catheterized conscious, spontaneously hypertensive rats (SHR/NiH—MO//CHB—EMD strain) the directly measured arterial blood pressure is lowered after intragastric administration of the active compounds (Methodology cf. Weeks and Jones, Proc. Soc. Exptl. Biol. Med. 104 (1960), 646–648).

On account of these results and investigations, it has been shown that the compounds of the formula I and their physiologically acceptable acid addition salts can be used as pharmaceutically active compounds, and also as intermediates for the preparation of further pharmaceutical active compounds.

The compounds of the formula I and their salts can be prepared by reacting a compound of the formula II

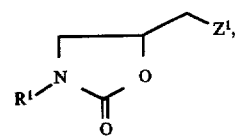

(II)

in which

R$^1$ has the meaning above and

Z$^1$ is Cl, Br, I, OH, alkylsulfonyloxy having 1–6 C atoms in the alkyl portion, arylsulfonyloxy having up to 60 C atoms in the aryl portion or another reactive functionally modified OH group, with a compound of the formula III

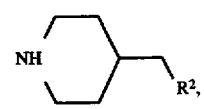

(III)

in which

R$^2$ has the meaning above or, when

Z$^1$ is NH$_2$, with a compound of the formula IIIa

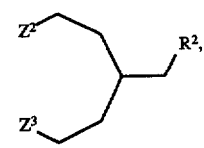

(IIIa)

in which

R$^2$ has the meaning above and $Z^2$ and $Z^3$ are identical or different and each are Cl, Br, I, OH, SO$_3$CH$_3$ or another reactive functionally modified OH group, in that a compound otherwise corresponding to the formula I, but which instead of one or more hydrogen atoms contains one or more reducible groups and/or one or more additional SO$_2$— and/or —SO— groups, is treated with a reducing agent, or in that for the preparation of a compound of the formula I according to claim 1 a radical $R^1$ and/or $R^2$ is converted into another radical $R^1$ and/or $R^2$, or in that a compound of the formula IV

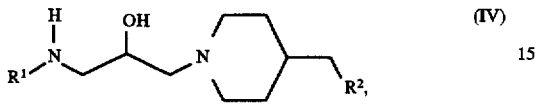

in which $R^1$ and $R^2$ have the meanings indicated above is reacted with a carbonic acid derivative and/or in that, if appropriate, a compound of the formula I is set free from one of its functional derivatives by treating with a solvolysing or hydrogenolysing agent, or a compound of the formula I is converted into another compound of the formula I by reduction or oxidation, and/or in that a base of the formula I is converted into one of its salts by treating with an acid.

Above and below, the radicals $R^1$, $R^2$, $R^3$, A and Hal and also the parameter n have the meanings indicated for formula I, if not expressly stated otherwise.

In the formulae or subformulae, A is an alkyl radical having 1–6 C atoms, preferably having 1, 2, 3 or 4 C atoms. In particular, A is methyl, ethyl, propyl, isopropyl, butyl, isobutyl, sec-butyl or tert-butyl, and furthermore also pentyl, 1-, 2- or 3-methyl-butyl, 1,1-, 1,2- or 2,2-dimethylpropyl, hexyl, 1-, 2- or 3-methylpentyl or else also 2,2- or 2,3- dimethyl-propyl.

The radicals $R^1$ and $R^2$ can be identical or different. $R^1$ and $R^2$ are preferably, in each case independently of one another, unsubstituted or substituted phenyl, where the possible substituents can be in the ortho, meta and, particularly preferably, in the para-position.

Specifically, $R^1$ and $R^2$ are preferably aryl, e.g., phenyl, naphthyl, or phenyl or naphthyl substituted by methyl, ethyl, tert-butyl, methoxy, ethoxy, fluorine, chlorine, hydroxyl, nitro, amino, alkylamino, in which alkyl has the meaning of A, acylamino, sulfonylamino, sulfonylimino, sulfonamido, p-phenylmethoxy, p-acetamidophenyl or p-N-methylacetamidophenyl. Phenyl is preferably substituted in the para-position.

Furthermore, $R^1$ and $R^2$ are also preferably 3,4-methylenedioxy-, propionylamido- or p-methylsulfonamidophenyl.

Acyl is, in particular, alkanoyl, e.g., acetyl, propionyl, but also formyl, butyryl, isobutyryl, valeryl, isovaleryl, pivaloyl (trimethylacetyl), and also optionally substituted aroyl having 7–13 C atoms, suitable substituents preferably being those from the following group: alkyl, alkoxy, alkylthio, alkylsulfinyl, or alkylsulfonyl having 1–3, preferably 1 or 2, C atoms, methylenedioxy, OH, F, Cl, Br, I, NO$_2$, NH$_2$, alkylamino or dialkylamino each having 1–3, preferably 1 or 2, C atoms in the alkyl group. Preferred aroyl radicals are benzoyl, o-, m- or p-toluoyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxy-benzoyl, o-, m- or p-methylsulfonylbenzoyl, 2,3- or 3,4-methylenedioxybenzoyl, 1- or 2-naphthoyl. Ac can furthermore be aralkanoyl having 1–10 C atoms such as, for example, phenylacetoyl, 2- or 3-phenylpropionyl or 2-, 3- or 4-phenylbutyryl or 2- or 3-phenylisobutyryl.

Accordingly, the invention also relates in particular to those compounds of the formula I in which at least one of the radicals mentioned has one of the meanings indicated, in particular those particularly indicated.

Some of the preferred groups of compounds can be expressed by the following subformulae, which correspond to the formula I, in which the radicals and parameters not designated in greater detail have the meanings indicated for the formula I, but in Ia $R^1$ is p-methoxyphenyl or phenyl and $R^2$ is p-acetamidophenyl;

in Ib $R^1$ is p-fluorophenyl and $R^2$ is p-acetamidophenyl;

in Ic $R^1$ is p-methoxyphenyl and $R^2$ is phenyl, m-methoxy-, p-methoxy-, p-hydroxy-, p-amino- p-chloro, p-fluoro-, p-phenylmethoxy-, 3,4-methylenedioxy-, p-methyl- or p-tert-butylphenyl;

in Id $R^1$ is p-methoxyphenyl, $R^2$ is p-methylsulfonamidophenyl in Ie $R^1$ is phenyl and $R^2$ is phenyl, m-methoxy-, p-methoxy-, p-hydroxy-, p-amino- p-chloro, p-fluoro-, p-phenylmethoxy-, 3,4-methylenedioxy-, p-methyl- p-tert-butyl- or p-methylsulfon-amidophenyl.

The preparation of the compounds of the formula I is otherwise carried out by methods known per se, such as are described in the literature (e.g. in the standard works such as Houben-Weyl, Methoden der Organischen Chemie [Methods of Organic Chemistry], Georg-Thieme-Verlag; J. March, Advanced Organic Chemistry 3rd Ed. (1984) or Organic Reactions, both John Wiley & Sons, Inc. New York), namely under reaction conditions such as are known and suitable for the reactions mentioned. Use can also be made in this case of variants which are known per se but not mentioned here in greater detail.

If desired, the starting substances for the process claimed can also be formed in situ in such a way that they are not isolated from the reaction mixture, but immediately reacted further to give the compounds of the formula I. In the compounds of the formula II, $Z^1$ is preferably Cl, Br, I, OH, alkylsulfonyloxy, arylsulfonyloxy or another reactive functionally modified OH group. Accordingly, the compounds of the formula II are reacted, in particular, with piperidine derivatives of the formula III in order to obtain compounds of the formula I. In particular, $Z^1$, when it is a reactive functionally modified OR group, is an alkylsulfonyloxy group having 1–6 C atoms, such as, for example, methanesulfonyloxy, or an arylsulfonyloxy group having up to 60 C atoms, such as, for example, benzene-sulfonyloxy, p-toluenesulfonyloxy, 1- or 2-naphthalene-sulfonyloxy.

However, it is also possible that $Z^1$ in compounds of the formula II is NH$_2$. The preparation of the compounds according to the invention therefrom is carried out by reacting with compounds of the formula IIIa in which $Z^2$ and $Z^3$ can be identical or different, preferably Cl or Br, but can also be I or OH or a reactive functionally modified OH group such as described above. The compounds of the formulae II, III and IIIa are in the main known from the literature. Previously unknown compounds of these structural formulae can be prepared in a simple manner analogously to the corresponding known compounds. Primary alcohols of the formula II are obtainable, for example, by reduction of the corresponding carboxylic acids or their esters. Treatment with thionyl chloride, hydrogen bromide, phosphorus tribromide or similar halogen compounds yields the corresponding halides of the formula II.

The sulfonyloxy compounds of the formula II are obtainable from the corresponding alcohols by reaction with the appropriate sulfonyl chlorides. The iodine compounds of the formula II are obtainable, for example, by action of potassium iodide on the associated p-toluenesulfonic acid esters. The amines of the formula II can be prepared, inter alia, from the halides using potassium phthalimide or by reduction of the corresponding nitriles., In general, the piperidines of the formula III are known. If corresponding previously unknown piperidines are needed for the preparation of a desired compound of the formula I, these can be prepared in analogy to the known compounds. Compounds of the formula IIIa can be prepared, for example, by reduction of corresponding diesters to diols and, if appropriate, subsequent reaction with $SOCl_2$ or $PBr_3$.

The reaction of the compounds II and III proceeds according to methods such as are known from the literature for the alkylation of amines. For example, the starting compounds can be fused directly with one another, to be specific, depending on their properties, if appropriate in a closed tube or in an autoclave. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, if appropriate also mixtures of these solvents with one another or mixtures with water. The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline or an excess of the amine component or the compound of the formula III or IIIa can be favorable. Depending on the conditions used, the reaction temperature is between approximately 0° and 150 C., normally between 20° and 130° C.

It is furthermore possible to obtain a compound of the formula I by treating a precursor which, instead of hydrogen atoms, contains one or more reducible groups and/or one or more additional C—C and/or C—N bonds, with a reducing agent, preferably at temperatures between –80° and 250° C. in the presence of at least one inert solvent.

Reducible (replaceable by hydrogen) groups are, in particular, oxygen in a carbonyl group, hydroxyl, arylsulfonyloxy (e.g. toluenesulfonyloxy), N-benzene-sulfonyl, N-benzyl or O-benzyl. P It is fundamentally possible to convert compounds which only contain one or those which together contain two or more of these groups or additional bonds into a compound of the formula I by reduction. Preferably, the catalytic hydrogenation of the nascent hydrogen or certain complex metal hydrides such as $NaBH_4$ or $LiAlH_4$ is used for this purpose.

Catalysts suitable for catalytic hydrogenation are, for example, noble metal, nickel and cobalt catalysts. The noble metal catalysts can be present on supports (e.g. platinum or palladium on carbon, palladium on calcium carbonate or strontium carbonate), oxide catalysts (e.g. platinum oxide) or as finely divided metal catalysts. Nickel and cobalt catalysts are expediently employed as Raney metals, nickel alternatively on kieselguhr or pumice as a support. The hydrogenation can be carried out at room temperature and normal pressure or alternatively at elevated temperature and/or elevated pressure. It is preferably carried out at pressures between 1 and 100 bar and at temperatures between –80° and +150° C., primarily between room temperature and 100° C. The reaction is expediently carried out in the acidic, neutral or basic range and in the presence of a solvent, such as water, methanol, ethanol, isopropanol, n-butanol, ethyl acetate, dioxane, acetic acid or THF, and mixtures of these solvents can also be employed.

If nascent hydrogen is used as the reducing agent, this can be generated, for example, by treating metals with weak acids or with bases. For example, a mixture of zinc and alkali metal hydroxide solution or of iron and acetic acid can thus be used. The use of sodium or of another alkali metal in an alcohol such as ethanol, isopropanol, butanol, amyl or isoamyl alcohol or phenol is also suitable. An aluminium-nickel alloy in alkaline-aqueous solution can furthermore be used, if appropriate with addition of ethanol. Sodium or aluminium amalgam in aqueous-alcoholic or aqueous solution is suitable for generation of the nascent hydrogen. The reaction can also be carried out in the heterogeneous phase, an aqueous and a benzene or toluene phase expediently being used.

The reducing agent employed can furthermore be complex metal hydrides, such as $NaBH_4$, diisobutylaluminium hydride or $NaAl(OCH_2CH_2OCH_3)_2H_2$ and also diborane, if desired with addition of catalysts such as $BF_3$, $AlCl_3$ or LiBr. Suitable solvents for this purpose are in particular ethers, such as diethyl ether, di-n-butyl ether, THF, dioxane, diglyme or 1,2-dimethoxyethane, and also hydrocarbons, such as benzene. For reduction with $NaBH_4$, alcohols such as methanol or ethanol, and furthermore water and also aqueous alcohols are primarily suitable as solvents. According to these methods, the reduction is preferably carried out at temperatures between –80° and +150° C., in particular between 0° and approximately 100° C.

Compounds of the formula I are furthermore obtainable by converting an aromatic radical $R^1$ and/or $R^2$ into another radical $R^1$ and/or $R^2$ by, for example, an electrophilic substitution.

Compounds of the formula I are furthermore obtainable by reaction of aminoalcohols of the formula IV with reactive derivatives of carbonic acid. Those suitable are preferably dialkyl carbonates such as dimethyl or diethyl carbonate, chloroformic acid esters such as methyl or ethyl chloroformate, N,N'-carbonyl-diimidazole or phosgene. The reaction expediently takes place in the presence of an inert solvent, preferably of a halogenated hydrocarbon such as chloroform, of a hydrocarbon such as toluene or of an amide such as DMF, at temperatures between approximately 20° and 200° C., preferably between 100° and 150° C. The carbonic acid derivative is expediently employed in an excess.

The compounds of the formula I can also be obtained by setting them free from their functional derivatives by solvolysis, in particular by hydrolysis, or by hydrogenolysis.

Preferred starting substances for the solvolysis or hydrogenolysis are those which otherwise correspond to the formula I, but instead of one or more free amino and/or hydroxy groups contain corresponding protected amino and/or hydroxy groups, preferably those which, instead of an H atom which is bonded to an N atom, carry an amino protective group, in particular those which, instead of an HN group, carry an $R^1$—N group in which $R^1$ is an amino protective group, and/or those which, instead of the H atom of a hydroxy group, carry a hydroxy protective group.

Several—identical or different—protected amino and/or hydroxy groups can also be present in the molecule of the starting substance. If the protective groups present are different from one another, in many cases they can be removed selectively.

The expression amino protective group is generally known and relates to groups which are suitable for protecting an amino group from chemical reactions, but which are easily removable after the desired reaction has taken place at the other position in the molecule. Typical groups of this type are in particular unsubstituted or substituted acyl, aryl (e.g. 2,4-di-nitrophenyl, aralkoxymethyl (e.g., benzyloxymethyl) or aralkyl groups (e.g. benzyl, 4-nitro-benzyl, triphenylmethyl). As the amino protective groups are removed after the desired reaction or reaction sequence, their nature and size is not critical; however, those having 1–20, in particular 1–8 C atoms are preferred. The expression "acyl group" is to be understood in the widest sense in connection with the present process. It includes acyl groups derived from aliphatic, araliphatic, aromatic or heterocyclic carboxylic acids or sulfonic acids, but in particular alkoxycarbonyl, aryloxycarbonyl and aralkoxycarbonyl groups. Examples of acyl groups of this type are alkanoyl such as acetyl, propionyl, butyryl; aralkanoyl such as phenacetyl; aroyl such as benzoyl or toluyl; aryloxyalkanoyl such as phenoxy-acetyl; alkoxycarbonyl such as methoxycarbonyl, ethoxy-carbonyl, 2,2,2-trichloroethoxycarbonyl, isopropoxy-carbonyl, tert-butoxycarbonyl, 2-iodoethoxycarbonyl; aralkoxycarbonyl such as benzyloxycarbonyl, 4-methoxy-benzyloxycarbonyl, 9-fluorenylmethoxycarbonyl. Preferred amino protective groups are tert-butoxycarbonyl, 2,4-dinitrophenyl, benzyloxymethyl, benzyloxycarbonyl, benzyl and acetyl.

The expression "hydroxy protective group" is likewise generally known and relates to groups which are suitable for protecting a hydroxy group from chemical reactions, but which are easily removable after the desired reaction has taken place at the other position in the molecule. Typical groups of this type are the abovementioned unsubstituted or substituted aryl, aralkyl or acyl groups, and furthermore also alkyl groups. In this case too, the nature and size of the hydroxy protective groups is not critical, as they are removed again after the desired chemical reaction or reaction sequence. However, protective groups having 1–20, in particular having 1–10, C atoms are preferred. Examples of hydroxy protective groups of this type are, inter alia, tert-butyl, benzyl, p-nitrobenzoyl, p-toluenesulfonyl and acetyl, benzyl and acetyl being particularly preferred.

The setting-free of the compounds of the formula I from their functional derivatives takes place, depending on the protective group used—e.g. using strong acids such as hydrochloric acid or sulfuric acid, strong carboxylic acids such as trichloroacetic acid or sulfonic acids such as benzene- or p-toluenesulfonic acid. This process can be carried out, if necessary, in the presence of an additional solvent.

Suitable inert solvents for this purpose are in particular organic solvents, i.e. carboxylic acids such as acetic acid, ethers such as tetrahydrofuran, amides such as dimethylformamide, halogenated hydrocarbons such as dichloromethane, and furthermore also alcohols such as methanol, ethanol or isopropanol and also water. However, mixtures of these solvents are also possible. Physiologically tolerable, inert solvents are preferably selected for this purpose, or those which, if the lowest residues are to remain in the prepared product, represent no health risk.

Trifluoroacetic acid is preferably used in an excess without addition of a further solvent. Perchloric acid, on the other hand, is used in a mixture of acetic acid and 70% perchloric acid in the ratio 9:1. The removal of the protective groups is expediently carried out at temperatures of approximately 0°–50° C., preferably at 15°–30° C. or room temperature.

Tert-butoxycarbonyl is preferably removed using 40% trifluoroacetic acid in dichloromethane or, if it cannot be carried out in another way, using approximately 3 to 5 n HCl in dioxane at 15°–60° C. 9-Fluorenyl-methoxycarbonyl groups are removed using an approximately 5–20% solution of dimethylamine, diethyl-amine or piperidine in DMF at 15°–50° C. Removal of 2,4-dinitrophenyl groups is carried out using an approximately 3–10% solution of 2-mercaptoethanol in DMF/water at 15°–30° C.

Hydrogenolytically removable protective groups, such as benzyloxymethyl, benzyloxycarbonyl or benzyl, can be removed by treating with hydrogen in the presence of a catalyst (e.g. noble metal catalyst such as palladium, expediently on a support such as carbon). Suitable solvents for this purpose are those indicated above, in particular alcohols such as methanol or ethanol or amides such as DMF. The hydrogenolysis is as a rule carried out at temperatures between 0° and 100° C. and pressures between 1 and 200 bar, preferably at 20°–30° C. and 1–10 bar. Hydrogenolysis of benzyloxy-carbonyl groups takes place, for example, readily on 5–10% Pd-C in methanol at 20° to 30° C.

If appropriate, a compound of the formula I can furthermore be converted by methods known per se into another compound of the formula I.

Appropriate ethers can thus be cleaved, the corresponding hydroxy derivatives being formed. Ethers of this type can also be cleaved by treating with a dimethyl sulfide-boron tribromide complex in a solvent such as toluene, 1,2-dichloroethane, THF or dimethyl sulfoxide or by fusing with pyridine or aniline hydrohalides. Preferably, this reaction is carried out using pyridine hydrochloride at approximately 150°–250° C., using HBr/acetic acid or using Al trihalides in chlorinated hydrocarbons such as 1,2-dichloroethane.

Compounds of the formula I can have a center of asymmetry. They can therefore be obtained as racemates or, if optically active starting compounds are employed, also in optically active form. If desired, racemates obtained can be resolved physically or chemically by methods known per se. Preferably, diastereomers are formed from the racemates by chemical reaction with an optically active resolving agent. Suitable resolving agents are, for example, optically active acids, such as the D- and L-forms of tartaric acid, dibenzoyltartaric acid, diacetyltartaric acid, camphorsulfonic acid, mandelic acid, malic acid or lactic acid. The various forms of the diastereomers can be separated in a manner known per se, e.g. by fractional crystallization, and the optically active compounds of the formula I set free from the diastereomers in a manner known per se.

A base of the formula I obtained can be converted into the associated acid addition salt using an acid. Suitable acids for this purpose are in particular acids which yield physiologically acceptable salts. Inorganic acids which can be used for this purpose are sulfuric acid, hydrohalic acids such as HCl, HBr, phosphoric acids such as orthophosphoric acid, nitric acid, sulfamic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid, acid addition salts which are physiologically unacceptable can be suitable for the isolation and purification of bases of the formula I.

If desired, the free bases of the formula I can be set free from their salts by treatment with strong bases such as sodium or potassium hydroxide, or sodium or potassium carbonate.

The compounds of the general formula I and their physiologically acceptable salts can therefore be used for the production of pharmaceutical preparations by bringing them into the suitable dose form together with at least one excipient or auxiliary and, if desired, with one or more further active compounds.

The preparations thus obtained can be employed as medicaments in human or veterinary medicine.

Possible excipients are organic or inorganic substances which are suitable for enteral (e.g. oral or rectal) or parenteral administration or topical application and do not react with the novel compounds, for example water, vegetable oils, benzyl alcohols, polyethylene glycols, gelatine, carbohydrates such as lactose or starch, cellulose, magnesium stearate, talc or petroleum jelly, glycerol triacetate and other fatty acid glycerides, soya lecithin.

Tablets, coated tablets, capsules, syrups, juices or drops are used in particular for oral administration. Coated tablets and capsules having enteric coatings or capsule shells are especially of interest. Suppositories are used for rectal administration, and solutions, preferably oily or aqueous solutions, and furthermore suspensions, emulsions or implants, for parenteral administration, and ointments, creams or powders for topical application.

The active compounds claimed according to the invention can also be lyophilized and the lyophilizates obtained used, for example, for the production of injection preparations.

The preparations indicated can be sterilized and/or contain auxiliaries such as lubricants, preservatives, stabilizers and/or wetting agents, emulsifiers, salts for affecting the osmotic pressure, buffer substances, colorants and/or flavorings. If desired, they can also contain one or more further active compounds, e.g. one or more vitamins, diuretics or anti-inflammatories.

The compounds of the formula I and their physiologically acceptable salts can be used for the therapeutic treatment of the human or animal body, in particular for the control of illnesses. They have neuro-protective action and therefore are all, to at least a finite extent, effective in the treatment of schizophrenia, of psycho-reactive disorders and psychopathies, depressions, severe chronic pain, and of illnesses which are associated with highblood pressure. The compounds can also be used in the treatment of extrapyramidal disorders. The compounds according to the invention are effective as atypical neuroleptics, but in this case advantageously do not show any noticeable cataleptic side effects.

The compounds of formula I according to the invention and their physiologically acceptable salts are generally administered in analogy to other known commercially available preparations for the indications claimed (thioridazine, haloperidol), preferably in doses between approximately 0.1 mg and 500 mg, in particular between 0.2 and 50 mg per dose unit. The daily dose is preferably between approximately 0.002 and 20 mg/kg, in particular 0.2 and 0.4 mg/kg, of body weight.

The specific dose for each individual patient, however, depends on all sorts of factors, for example on the efficacy of the specific compound employed, on the age, body weight, general state of health, sex, on the diet, on the time and route of administration, on the excretion rate, pharmaceutical substance combination and severity of the particular disorder to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 31 321.6, filed Aug. 25, 1995, are hereby incorporated by reference.

In the examples below, "customary" working-up means: if necessary, water is added, the mixture is extracted with dichloromethane, the organic phase is separated off, dried over sodium sulfate, filtered and evaporated, and the residue is purified by chromatography on silica gel and/or by crystallization. The $[\alpha]_D$ values are measured at 20° C. in dimethyl sulfoxide.

EXAMPLES

Example 1

A solution consisting of 4.92 g of (5R)-(−)-5-(methanesulfonyloxymethyl)-3-p-fluorophenyloxazolidin-2-one, 65 ml of acetonitrile, 4.70 g of 4-(4-aminobenzyl)piperidine [can be prepared from 4-(4-nitrobenzyl)pyridine by hydrogenation of the nitro group to $NH_2$ and of the pyridine ring to the piperidine ring in the presence of a palladium catalyst in glacial acetic acid] and 4.43 g of sodium hydrogen carbonate is stirred under reflux conditions for a period of 26 hours. The reaction mixture is then diluted with 100 ml of dichloromethane, extracted several times with small amounts of water and dried. After drying, the solvent is distilled off and the product obtained is purified by chromatography on a silica gel column. In this way, the reaction product is obtained as a colourless resin which is crystallized.

Yield: 3.18 g of (5S)-(−)-5-[4-(4-aminobenzyl)-1-piperidinylmethyl]-3-(4-fluorophenyl)-oxazolidin-2-one (48.8% of theory), m.p. 95°–99° C.

$[\alpha]_D^{20}=-24.5°(DMSO)$

The following can be prepared analogously from 4-(4-acetylaminobenzyl)piperidine

[can be prepared from 4-(4-nitrobenzyl)pyridine by hydrogenation of the nitro group to $NH_2$ in the presence of a nickel catalyst (Raney nickel) to give 4-(4-aminobenzyl)pyridine, acetylation with acetic anhydride/triethylamine to give 4-(acetylaminobenzyl)pyridine and subsequent hydrogenation of the pyridine ring in the presence of a palladium catalyst in glacial acetic acid]

and (5R)-(−)-5-(methanesulfonyloxymethyl)-3-(p-fluorophenyl)oxazolidin-2-one (5S)-(−)-5-[4-(4-acetylaminobenzyl)-1-piperidinyl-methyl]-3-(4-fluorophenyl)oxazolidin-2-one M.P. 177°–179° C.
[α]$_D^{20}$=−23.6°(DMSO)
from 4-(4-fluorobenzyl)piperidine
and (5R)-(−)-5-(methanesulfonyloxymethyl)-3-(4-methoxyphenyl)oxazolidin-2-one
(5S)-(−)-5-[4-(4-fluorobenzyl)piperidinylmethyl]-3-(4-methoxyphenyl)oxazolidin-2-one
M.P. 203°–205° C.
[α]$_D^{20}$=−27.7°(DMSO)
from 4-( 4-acetylaminobenzyl)piperidine
and (5R)-(−)-5-(methanesulfonyloxymethyl)-3-(4-methoxyphenyl)oxazolidin-2-one
(5S )-(−)-5-[4-(4-acetylaminobenzyl)-1-piperidinylmethyl]-3-(4-methoxyphenyl)oxazolidin-2-one
M.p. 204°–206° C.
[α]$_D^{20}$=−25.8°(DMSO)
from 4-(4-aminobenzyl) piperidine
and (5R)-(−)-5-(methanesulfonyloxymethyl)-3-(4-methoxyphenyl)oxazolidin-2-one
(5S)-(−)-5-[4-(4-aminobenzyl)-1-piperidinylmethyl]-3-(4-methoxyphenyl)oxazolidin-2-one
M.p. 126°–128° C.
[α]$^{D20}$32 −27.8°(DMSO)
from 4-(4-acetylaminobenzyl)piperidine
and (5R)-(−)-5-(methanesulfonyloxymethyl)-3-phenyl-oxazolidin-2-one
M.p. 199°–201° C.
[α]$_D^{20}$=−24.3°(DMSO)
from 4-(4-acetylaminobenzyl)piperidine
and (5R)-(−)-5-(methanesulfonyloxymethyl)-3-(4-chlorophenyl)oxazolidin-2-one
(5S)-(−)-5-[4-(4-acetylaminobenzyl)-1-piperidinylmethyl]-3-(4-chlorophenyl)oxazolidin-2-one
M.p. 221°–223° C.
[α]$_D^{20}$=−27.4°(DMSO)
from 4 -(4-aminobenzyl)piperidine
and (5R) -(−)-5-(methanesulfonyloxymethyl)-3-(4-chlorophenyl)oxazolidin-2-one
(5S)-(−)-5-[4-(4-aminobenzyl)-1-piperidinylmethyl]-3-(4-chlorophenyl)oxazolidin-2-one
M.p. 146°–149° C.
[α]$_D^{20}$ =−29.8°(DMSO)
from 4-(4-aminobenzyl)piperidine
and (5R)-(−)-5-(methanesulfonyloxymethyl)-3-phenyloxazolidin-2-one
(5S)-(−)-5-[4-(4-aminobenzyl)-1-piperidinylmethyl]-3-phenyloxazolidin-2-one
M.p. 148°–150° C.
[α]$_D^{20}$=−28.5°(DMSO)

The following examples relate to pharmaceutical preparations:

Example A: Injection vials

A solution of 100 g of an active compound of the formula I and 5 g of disodium hydrogen phosphate are [sic] adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of double-distilled water. The mixture is adjusted to pH 6.8, made up to 1 l and sterilized by irradiation.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.28 kg of talc and 0.1 kg of magnesium stearate is compressed to give tablets in a customary manner such that each tablet contains 10 mg of active compound.

Example F: Coated tablets

Analogously to Example E, tablets are pressed which are then coated in a customary manner with a coating of sucrose, potato starch, talc, tragacanth and colorant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A piperidinyl methyloxazolidin-2-one compound of formula I

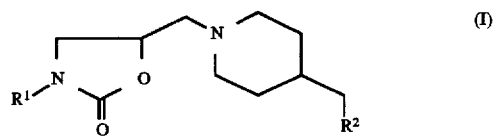

in which

R$^1$ and R$^2$ are each independently phenyl mono- or disubstributed by C$_{6-10}$-aryloxy, C$_{7-11}$-aralkyloxy, —O—(CH$_2$)$_n$—O— which is bonded in directly adjacent positions or in the meta- or para-position to one another on the phenyl ring, —O—(CH$_2$)$_n$—OH, Hal, CF$_3$, OH, NO$_2$, NH$_2$, NHA, NA$_2$, NHR$^3$, NAR$^3$, SO$_2$NH$_2$, SO$_2$NHA, SO$_2$NA$_2$, SO$_2$NHR$^3$, SO$_2$N(R$^3$)$_2$ or R$^3$, R$^3$ is COH, CO—C$_{1-7}$-alkyl, CO-alkyl-aryl having 8–12 C atoms in the alkyl and aryl portions, CO—C$_{7-15}$-aryl or SO$_2$A, A is C$_{1-6}$-alkyl, n is 1 or 2, and Hal is F, Cl, Br or I, or a physiologically acceptable salt thereof, with the proviso that in SO$_2$NHR$^3$ and SO$_2$N(R$^3$)$_2$, R$^3$ is not SO$_2$A.

2. A compound according to claim 1, wherein A is methyl, ethyl, propyl, isopropyl, butyl, isobutyl, sec-butyl or tert-butyl.

3. A compound according to claim 1, wherein R$^1$ and R$^2$ are phenyl substituted in the para-position by fluorine, chlorine, hydroxyl, nitro, amino, alkylamino, in which alkyl has the meaning of A, acylamino, sulfonylamino, sulfonylimino, sulfonamido, p-phenylmethoxy, p-acetamidophenyl, p-N-methylacetamidophenyl, 3,4-methylenedioxy-, propionylamido- or p-methylsulfonamidophenyl.

4. A compound according to claim 3, wherein acyl is alkanoyl or $C_{1-10}$-aralkanoyl.

5. A compound according to claim 1, wherein in Ia $R^2$ p-acetamidophenyl;

in Ib $R^2$ is p-fluorophenyl and
$R^2$ is p-acetamidophenyl;

in Ic $R^2$ is p-hydroxy-, p-amino-, p-chloro-, p-fluoro-, p-phenylmethoxy-, or 3,4-methylenedioxy-;

in Id $R^2$ is p-methylsulfonamidophenyl; and in Ie $R^2$ is p-hydroxy-, p-amino-, p-phenylmethoxy-, 3,4-methylenedioxy- or p-methylsulfonamidophenyl.

6. A compound according to claim 1, which is a) (5S)-(−)-5-[4-(4-aminobenzyl)-1-piperidinylmethyl]-3-(4-fluorophenyl)oxazolidin-2-one, b) (5S)-(−)-5-[4-(4-acetylaminobenzyl)-1-piperidinylmethyl]-3-(4-fluorophenyl)oxazolidin-2-one, c) (5S)-(−)-5-[4-(4-acetylaminobenzyl)-1-piperidinylmethyl]-3-(4-chlorophenyl)oxazolidin-2-one, or d) (5S)-(−)-5-[4-(4-aminobenzyl)-1-piperidinylmethyl]-3-(4-chlorophenyl)oxazolidin-2-one.

7. A process for the preparation of a piperidinylmethyloxazolidin-2-one compound of formula I according to claim 1, or a salt thereof, comprising reacting a compound of formula II

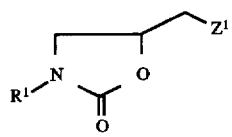

in which $Z^1$ is Cl, Br, I, OH, $C_{1-6}$-alkyl-sulfonyloxy, arylsulfonyloxy having up to 60 C atoms in the aryl portion or a reactive functionally modified OH group, with a compound of formula III

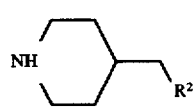

or (b) if $Z^1$ is $NH_2$, reacting a compound of formula II with a compound of the formula IIIa

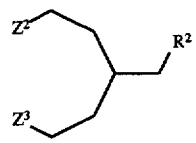

in which $Z^2$ and $Z^3$ are each independently Cl, Br, I, OH, $SO_3CH_3$ or a reactive functionally modified OH group, or (c) heating a compound otherwise corresponding to formula I but in which one or more hydrogen atoms are replaced by one or more reducible groups and/or one or more additional $SO_2$— and/or —SO— groups, with a reducing agent, or (d) in a compound of formula I converting a group $R^1$ and/or $R^2$ into another group $R^1$ and/or by electrophilic substitution, or cleaving of an ether to form a hydroxy group, or (e) reacting a compound of formula IV

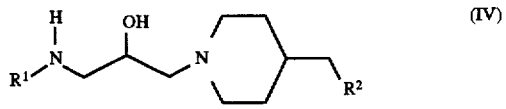

with a carbonic acid or (f) liberating a compound of formula I from a functional compound thereof by treating with a solvolyzing or hydrogenolyzing agent, or (g) converting a compound of formula I into another compound of formula I by reduction or oxidation, or (h) converting a base of formula I into a salt thereof by treating with an acid.

8. A process for the production of a pharmaceutical composition comprising bringing a compound of the formula I according to claim 1 and/or a physiologically acceptable salt thereof into a suitable dose form together with at least one solid, liquid or semiliquid excipient and/or auxiliary.

9. A pharmaceutical composition comprising at least one compound of formula I according to claim 1 and/or a physiologically acceptable salt thereof and a pharmaceutically acceptable carrier.

10. A method of treating high blood pressure, pain, schizophrenia, a psychoreactive disorder, depression or an extrapyramidal disorder comprising administering a compound of claim 1.

11. A piperidinyl methyloxazolidin-2-one compound of formula I

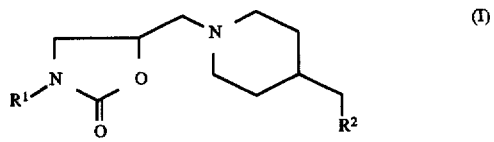

in which $R^1$ and $R^2$ are each independently phenyl mono- or disubstituted by $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, $NO_2NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$, $R^3$ is COH, CO—$C_{1-7}$-alkyl, CO-alkyl-aryl having 8–12 C atoms in the alkyl and aryl portions, CO—$C_{7-15}$-aryl or $SO_2A$, A is $C_{1-6}$-alkyl, n is 1 or 2, and or a physiologically acceptable salt thereof, with the proviso that in $SO_2NHR^3$ and $SO_2N(R^{3\prime})_2$, $R^3$ is not $SO_2A$.

12. A compound according to claim 1, wherein $R^1$ and $R^2$ are phenyl substituted in the para-position by nitro, amino, alkylamino, in which alkyl has the meaning of A, acylamino, sulfonylamino, sulfonylimino, sulfonamido, p-phenylmethoxy, p-acetamido-phenyl, p-N-methylacetamidophenyl, 3,4-methylenedioxy-, propionylamido- or p-methylsulfonamidophenyl.

13. A compound according to claim 4, wherein acyl is acetyl, propionyl, formyl, butyryl, isobutyryl, valeryl, isovaleryl, pivaloyl, or aroyl optionally substituted by alkyl, alkoxy, alkylthio, alkylsulfinyl or alkylsulfonyl having 1–3 C atoms in the alkyl group.

14. A piperidinyl methyloxazolidin-2-one compound of formula I

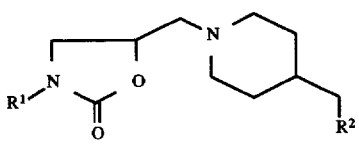

(I)

in which

R$^1$ is phenyl optionally mono- or disubstituted by A, OA, $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$, R$^2$ is phenyl mono- or di-substituted by A, OA, $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$, R$^3$ is COH, CO—$C_{1-7}$-alkyl, CO-alkyl-aryl having 8–12 C atoms in the alkyl and aryl portions, CO—$C_{7-15}$-aryl or $SO_2A$, A is $C_{1-6}$-alkyl, n is 1 or 2, and Hal is F, Cl, Br or I, or a physiologically acceptable salt thereof, with the proviso that in $SO_2NHR^3$ and $SO_2N(R^3)_2$, $R^3$ is not $SO_2A$.

15. A compound according to claim 14, wherein $R^2$ is phenyl mono- or disubstituted by $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$.

16. A compound according to claim 14, wherein $R^1$ is phenyl mono- or disubstituted by A, OA, $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$.

17. A compound according to claim 14, wherein $R^1$ is phenyl mono- or disubstituted by $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, Hal, $CF_3$, OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$.

18. A compound according to claim 14, wherein $R^1$ is phenyl mono- or disubstituted by $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, $NO_2$, $NH_2$, NHA, $NA_2$ $NHR^3$, $NAR^3$, $SO_2NH_2$, $SO_2NHA$, $SO_2NA_2$, $SO_2NHR^3$, $SO_2N(R^3)_2$ or $R^3$.

19. A compound according to claim 14, wherein $R^2$ is phenyl mono- or disubstituted by $C_{6-10}$-aryloxy, $C_{7-11}$-aralkyloxy, —O—$(CH_2)_n$—O— which is bonded in directly adjacent positions or in the meta- or para-position to one another on the phenyl ring, —O—$(CH_2)_n$—OH, $NO_2$, $NH_2$, NHA, $NA_2$, $NHR^3$, $NAR^3$, $SO_2NH_2$, $SO_2NHA$, $SO_2NA_2$, $SO_2NHR^3$, $SO_2N(R^3)_2$ or $R^3$.

* * * * *